US005959180A

United States Patent [19]
Moehs et al.

[11] Patent Number: 5,959,180
[45] Date of Patent: Sep. 28, 1999

[54] DNA SEQUENCES FROM POTATO ENCODING SOLANIDINE UDP-GLUCOSE GLUCOSYLTRANSFERASE AND USE TO REDUCE GLYCOALKALOIDS IN SOLANACEOUS PLANTS

[75] Inventors: Charles P. Moehs, El Cerrito; Paul V. Allen, Pinole; David R. Rockhold, Oakland; Andrew Stapleton, Martinez; Mendel Friedman, Moraga; William R. Belknap, Albany, all of Calif.

[73] Assignee: The United States of America as represented by the Secretary of Agriculture, Washington, D.C.

[21] Appl. No.: 08/797,226

[22] Filed: Feb. 7, 1997

[51] Int. Cl.[6] .............................. A01H 5/00; C12N 5/14; C12N 15/29; C12N 15/51
[52] U.S. Cl. ..................... 800/298; 435/320.1; 435/419; 435/468; 536/23.2; 536/23.6; 800/278; 800/286; 800/317.2; 800/317.4
[58] Field of Search ................................. 536/23.2, 23.6; 435/172.3, 320.1, 419, 254.2, 252.3, 468; 800/205, DIG. 40, DIG. 42, DIG. 44, 278, 286, 298, 317.2, 317.4

[56] References Cited

U.S. PATENT DOCUMENTS

| | | | |
|---|---|---|---|
| 5,352,605 | 10/1994 | Fraley et al. | 435/240.4 |
| 5,614,408 | 3/1997 | Stanker et al. | 435/341 |

OTHER PUBLICATIONS

C. Paczkowski et al., "UDP–Glucose: Solasodine Glucosyltransferase from Eggplant (*Solanum melongena* L.) Leaves: Partial Purification and Characterization," Acta Biochimical Polonica 44(1):43–54 (1997) (Abstract) (BIOSIS, An 97:309475).

Horvath DM, et al. "Identification of an immediate–early salicyclic acid–inducible tobacco gene and characterization of induction by other compounds." Plant Mol. Biol. 31: 1061–1072, 1996.

Horvath DM, et al. GenBank Accession No. U32644, 1995.

Moehs, C.P. et al., "Cloning and expression of solanidine UDP–glucose glucosyltransferase from potato", The Plant Journal (1997), vol. 11(2):227–236.

Friedman, M. and G.M. McDonald, "Potato Glycoalkaloids: Chemistry, Analysis, Safety, and Plant Physiology", Critical Reviews in Plant Sciences (1997), vol. 16(1):55–132.

Moehs, C.P., et al., "Cloning of solanidine UDP–glucose glucosyltransferase from potato by functional expression in yeast", Phytochemical Society of North America (Jul. 1996), vol. 36, p. 11.

Snyder, G.W. and W.R. Belknap, "A modified method for routine Agrobacterium–mediated transformation of in vitro grown potato microtubers", Plant Cell Reports (1993), vol. 12:324–327.

Friedman, M. and C.E. Levin, "Reversed–phase high–performance liquid chromatographic separation of potato glycoalkaloids and hydrolysis products on acidic columns", J. Agric. Food Chem. (1992), vol. 40:2157–2163.

Bergenstrahle, A., et al., "Regulation of glycoalkaloid accumulation in potato tuber discs", J. Plant Physiol. (1992), vol 140:269–275.

Berenstrahle, A., et al., "Characterization of UDP–glucose: solanidine glucosyltransferase and UDP–galactose: solanidine galactosyltransferase from potato tuber", Plant Science (1992), vol. 84:35–44.

van der Steege, G., et al., "Potato granule–bound starch synthase promoter–controlled GUS expression: regulation of expression after transient and stable transformation", Plant Molecular Biology (1992), vol. 20:19–30.

Stapleton, A., et al, "Partial amino acid sequence of potato solanidine UDP–glucose glucosyltransferase purified by new anion–exchange and size exclusion media", Protein Expression and Purification (1992), vol. 3(2):85–92.

Stapleton, A., et al., "Purification and characterization of solanidine glycosyltransferase from the potato (*Solanum tuberosum*)", Journal of Agricultural & Food Chemistry (Jun. 1991), vol. 39(6):1187–1193.

Visser, R.G.F., et al., "Expresion of a chimaeric granule–bound starch synthase–GUS gene in transgenic potato plants", Plant Molecular Biology (1991), vol. 17:691–699.

van der Leij, F.R., et al., "Sequence of the structural gene for granule–bound starch synthase of potato (*Solanum tuberosum* L.) and evidence for a single point deletion in the amf allele", Mol. Gen. Genet. (1991), vol. 228:240–248.

McBride, K.E. and K.R. Summerfelt, "Improved binary vectors for Agrobacterium–mediated plant transformation", Plant Molecular Biology (1990), vol. 14:269–276.

Delauney, A.J., et al., "A Stable bifunctional antisense transcript inhibiting gene expression in transgenic plants", Proc. Natl. Acad. Sci. USA (Jun. 1988), vol. 85:4300–4304.

Sanders, P.R., et al., "Comparison of cauliflower mosaic virus 35S and nopaline synthase promoters in transgenic plants", Nucleic Acids Research (1987), vol. 15(4):1543–1558.

Ecker, J.R. and R.W. Davis, "Inhibition of gene expression in plant cells by expression of antisense RNA", Proc, Natl. Acad. Sci. USA (Aug. 1986), vol. 83:5372–5376.

Fitzpatrick, T.J. and S.F. Osman, "A comprehensive method for the determination of total potato glycoalkaloids", American Potato Journal (1974), vol. 51:318–323.

*Primary Examiner*—Lynette F. Smith
*Assistant Examiner*—Amy J. Nelson
*Attorney, Agent, or Firm*—M. Howard Silverstein; Curtis P. Ribando; Nancy J. Parsons

[57] ABSTRACT

DNA sequences from potato which encode the enzyme solanidine UDP-glucose glucosyltransferase (SGT) are disclosed. Recombinant DNA molecules containing the sequences, and use thereof, in particular, use of an antisense DNA construct to inhibit the production of SGT and thereby reduce glycoalkaloid levels in solanaceous plants, e.g., potato, are described.

14 Claims, 8 Drawing Sheets

Figure 2A

```
TGG TTG CCA GTT GGT AAT TTA GAG GAC AAG ACT AAA AAG GGT TTG TAC ATC AAA GGG TGG GTC CCA CAG CTT ACG ATC   357
 W   L   P   V   G   N   L   E   D   K   T   K   K   G   L   Y   I   K   G   W   V   P   Q   L   T   I

ATG GAA CAT TCA GCA ACA GGC GGG TTC ATG ACT CAT TGT GGT ACT AAT TCG GTT CTG GAA GCC ATC ACT TTT GGC GTG   383
 M   E   H   S   A   T   G   G   F   M   T   H   C   G   T   N   S   V   L   E   A   I   T   F   G   V

CCA ATG ATA ACA TGG CCA CTT TAT GCT GAT CAA TTC TAC AAC GAG AAG GTA GTC GAG GTT AGG GGA ATC AAA           409
 P   M   I   T   W   P   L   Y   A   D   Q   F   Y   N   E   K   V   V   E   V   R   G   I   K

ATC GGG ATA GAT GTA ATC AGT AAT GAA GGT TCT TCG TGG AAC AAT CTC ACT GCT CTC ATT CAA CAT ATC AAG AAT CTT   435
 I   G   I   D   V   I   S   N   E   G   S   S   W   N   N   L   T   A   L   I   Q   H   I   K   N   L

GAG AGA CTA ATG ACA AAT GAA ATA AGT AAT GAA GGT TCT GGA TCT GGA GGG ATA AGT CCT TGC ATT GTA ACA TGG TGT GTG TTT TTT TTC CAC TTA ATA AAA TGA   461
 E   R   L   M   T   N   E   I   S   N   E   G   S   G   S   G   G   I   S   P   C   I   V   T   W   C   V   F   F   F   H   L   I   K

CAG AAT GCA ACA GAA ATA AGT CCT TGC ATT GTA ACA TGG TGT GTG TTT TTT TTC CAC TTA ATA AAA TGA             487
 Q   N   A   T   E   I   S   P   C   I   V   T   W   C   V   F   F   F   H   L   I   K

AAT TAG TTG AAG ACA GAA ATA AGT CCT TGC ATT GTA ACA TGG TGT GTG TTT TAA CTT TAA AAA AAA AAA AAA A
 N

AGG AAT GGA TGG ATG GAT GGA TCT TAA
```

Figure 2B

```
StSGT  12  HVLFLPFLSAGHFIPLVNAARLFASRGVKATHTT
PhART   9  HVVMFPFAFGHISPEVQLANKLSSYGVKVSFFTA
IAAGT   4  HVLVVPFPGOGHMNPMVQFAKRLASKGVATHVTT
ParRT   2  HALLAIGSAGDVFPFIGLARTLKLRGHRVSLCTI
```

Figure 3

| | | |
|---|---|---|
| StSGT | 351 | WVPQLTIMEHSATGGFMTHCGTNSVLEAITFGVPMITWPLYADQFYNEKVV |
| CasGT | 351 | WSPQIHIMSHPSVGVFLSHCGWNSVLESITAGVPIIAWPIYAEQRMNATLL |
| IAAGT | 341 | WCPQLDVTAHEAVGCFVTHCGWNSTLEALSFGVPMVAMALWTDQPTNARNV |
| PhART | 341 | WVQQHILAHSSVGCYVCHAGFSSVIEALVNDCQVMLPQKGDQILNAKLV |
| MzBz1 | 351 | WAPQVAVLRHPSVGAFVTHAGWASVLEGVSSGVPMACRPFFGDQRMNARSV |

Figure 4

```
StSGT   110  KPMEDKIRELRPDCIFSDMYFPWTVDIADELHIP
Hudb7   134  KKFMKKVQESRFDVIFADAIFPCSELIAELFNIP
Hudbb   134  KKTMKKIQESRFDVLADAVFPEGELIAELLKIP
Rudb6   135  KQTMAKIQESKFDVLLSDPVAACGELIAEVLHIP
```

Figure 5

DNA SEQUENCES FROM POTATO ENCODING SOLANIDINE UDP-GLUCOSE GLUCOSYLTRANSFERASE AND USE TO REDUCE GLYCOALKALOIDS IN SOLANACEOUS PLANTS

BACKGROUND OF THE INVENTION

1. Field of the Invention

The present invention relates to the enzyme solanidine UDP-glucose glucosyltransferase (SGT) which is involved in the biosynthesis of steroidal glycoalkaloids in solanaceous plants. More particularly, the invention relates to DNA sequences which encode SGT, recombinant polynucleotide molecules containing the sequences, and use thereof, in particular, use of an antisense DNA construct to inhibit SGT activity and glycoalkaloid levels in solanaceous plants.

2. Description of the Art

Solanaceous plants include such agronomically important crops as potato and tomato. Solanaceous species synthesize steroidal glycoalkaloids (nitrogen-containing steroidal glycosides) which are natural toxicants and are believed to serve as natural defenses against insect and other pests. These compounds can exhibit toxic effects in humans as well as insects, and thus represent a potential source of toxicants, especially in improperly stored or processed potatoes. This has led to the implementation of a guideline limiting glycoalkaloid content in a tuber of a given potato cultivar to 20 mg/100 gm. Worldwide, between 13 and 27% of the potato crop has to be discarded because glycoalkaloid levels are above the maximum currently deemed to be safe (Morris and Lee, Food Technol. Aust. 36: 118–124 (1984)). While the guideline provides effective protection for the consumer, its effectiveness is dependent upon limiting the release of new cultivars for commercial production to those with acceptable glycoalkaloid levels. For potato breeding programs to develop new cultivars with improved agronomic or processing properties, the need to select also for low levels of glycoalkaloids can present a difficult problem. A method to decrease the glycoalkaloid content of any newly developed cultivar with minimum impact on other characteristics would be of great use to obtain valuable new commercial potato cultivars.

In cultivated potato the predominant glycoalkaloid species, α-chaconine and α-solanine, are triglycosylated derivatives of the aglycon solanidine. These steroidal glycoalkaloids (SGAs) contain either glucose (α-chaconine) or galactose (α-solanine) as the primary glycosyl residue. A simplified biochemical pathway illustrating biosynthesis of the toxic glycoalkaloids α-chaconine and α-solanine is shown in FIG. 1. The synthesis of γ-chaconine (3-β-O-glucosylsolanidine), an intermediate in the pathway to α-chaconine, is catalyzed by SGT. The activity and kinetics of the enzyme SGT have been characterized by a number of groups (Stapleton et al., J. Agric. Food Chem. 39:1187–1193 (1991); Bergenstrahle et al., Plant Sci. 84:35–44 (1992); Zimowski, Phytochemistry 6:1827–1831 (1991); Packowski and Wojciechowski, Phytochemistry 35:1429–1434 (1994)). The aglycone portion of the glycoalkaloid is believed to be considerably less toxic than the glycoside. It is believed that decreasing the activity of the enzyme(s) responsible for glycosylation of the aglycone should effectively lower the potential toxicity of potato cultivars.

A biosynthetic pathway to solanidine has been proposed (Kaneko et al., Phytochemistry 15: 1391–1393 (1976), E. Heftmann, Phytochemistry 22: 1843–1860 (1983)). Information on the enzymatic mechanisms involved in the glycosylation steps of solanidine to form glycoalkaloids is limited to reports utilizing relatively crude enzyme preparations (D. R. Liljegren, Phytochemistry 10: 3061–3064 (1971), Jadhav et al., Journal of Food Science 38: 1099 (1973), Lavintman et al., Plant Science Letters 8: 65–70 (1977), Osman et al., Phytochemistry 19: 2599–2601 (1980), J. Zimowski, Phytochemistry 30: 1827–1831 (1991)). Stapleton et al., 1991, supra, reported a 600-fold purification of a monomeric, 36- to 38-kilodalton (kDa), soluble protein, SGT from potato sprouts. SGT was isolated by anion-exchange ("Mono Q"), size exclusion ("Superose" 12), and chromatofocusing ("Mono P"). This purification protocol resulted in a very low yield of SGT. A major difficulty encountered was the copurification of SGT with patatin. Patatin is an approximately 40-kDa glycoprotein which can constitute up to 40% of the soluble potato tuber protein.

SUMMARY OF THE INVENTION

The present invention comprises DNA sequences in isolated and purified form which encode the enzyme solanidine UDP-glucose glucosyltransferase (SGT). DNA sequences which hybridize specifically to a SGT coding sequence or its complement under stringent conditions are also encompassed by the present invention. Methods to obtain the sequences are also disclosed herein.

A further aspect of the invention is the provision of recombinant DNA molecules containing the sequences. Such molecules include, for example, recombinant vectors, such as cloning or expression vectors, which contain a DNA sequence encoding SGT.

Another aspect of the invention is the provision of cells which are transformed by the above vectors or DNA sequences.

A further aspect of the present invention is provision of antisense DNA sequences which are capable of being transcribed to form RNA to inhibit the production of SGT.

A particular use of the invention is the provision of plants or plant cells transformed with an antisense nucleotide sequence complementary to an mRNA-encoding SGT, to provide plants having reduced levels of glycoalkaloids.

A still further aspect of the invention is the provision of oligonucleotide probes capable of detecting the gene for SGT or fragment thereof and use of the probes to isolate DNA sequences encoding SGT. The DNA sequences which hybridize to the probes are encompassed by the present invention.

Another aspect of the invention is the provision of methods to obtain purified SGT. SGT is present in potato cultivars in an extremely low level, is inherently unstable, and copurifies with the major storage protein during isolation.

The invention represents the first successful cloning of SGT. One of the primary advantages of the invention is that it can provide a method to reduce toxic glycoalkaloid concentrations in solanaceous species. Such a method offers a wide variety of benefits extending from the farm, to processing, shipping, and finally to marketing of potatoes and potato products. The ability to reduce toxicant levels in selected varieties will allow introduction of new potato cultivars which cannot currently be released due to glycoalkaloid concentrations exceeding the acceptable level. The utilization of direct genetic modification is especially important to avoid problems of classic potato breeding programs. The genome of commercial potato cultivars grown in the United States (which are tetraploid and highly heterozygous) is exceedingly complex. This genetic complexity makes it essentially impossible for breeders to introduce a single genetic trait into an existing cultivar, while maintaining its original properties. The invention provides a means to insert a sense or antisense SGT transgene into the genome of these cultivars without altering the existing genes.

Another advantage of the invention is that it provides a means of solving problems in potato storage and shipping due to glycoalkaloids. Inappropriate post-harvest handling of tubers can result in increased glycoalkaloid biosynthesis in current commercial cultivars. The inactivation of glycoalkaloid biosynthetic pathways is beneficial to reduce or eliminate glycoalkaloid biosynthesis during storage and shipping.

Other objects and advantages of this invention will become readily apparent from the ensuing description.

BRIEF DESCRIPTION OF THE DRAWINGS

FIGS. 2A and 2B show the nucleotide and deduced amino acid sequence of the potato SGT cDNA clone.

FIG. 3 shows a comparison of the amino acid sequences of the amino terminal domains of UDP-glycosyltransferases.

FIG. 4 shows a comparison of the amino acid sequences of the UDP binding domain of UDP-glycosyltransferases.

FIG. 5 shows a comparison of a putative steroid-binding domain of three steroid-specific mammalian UDP-glucuronosyltransferases and potato SGT (StSGT).

DETAILED DESCRIPTION OF THE INVENTION

Figure 1:
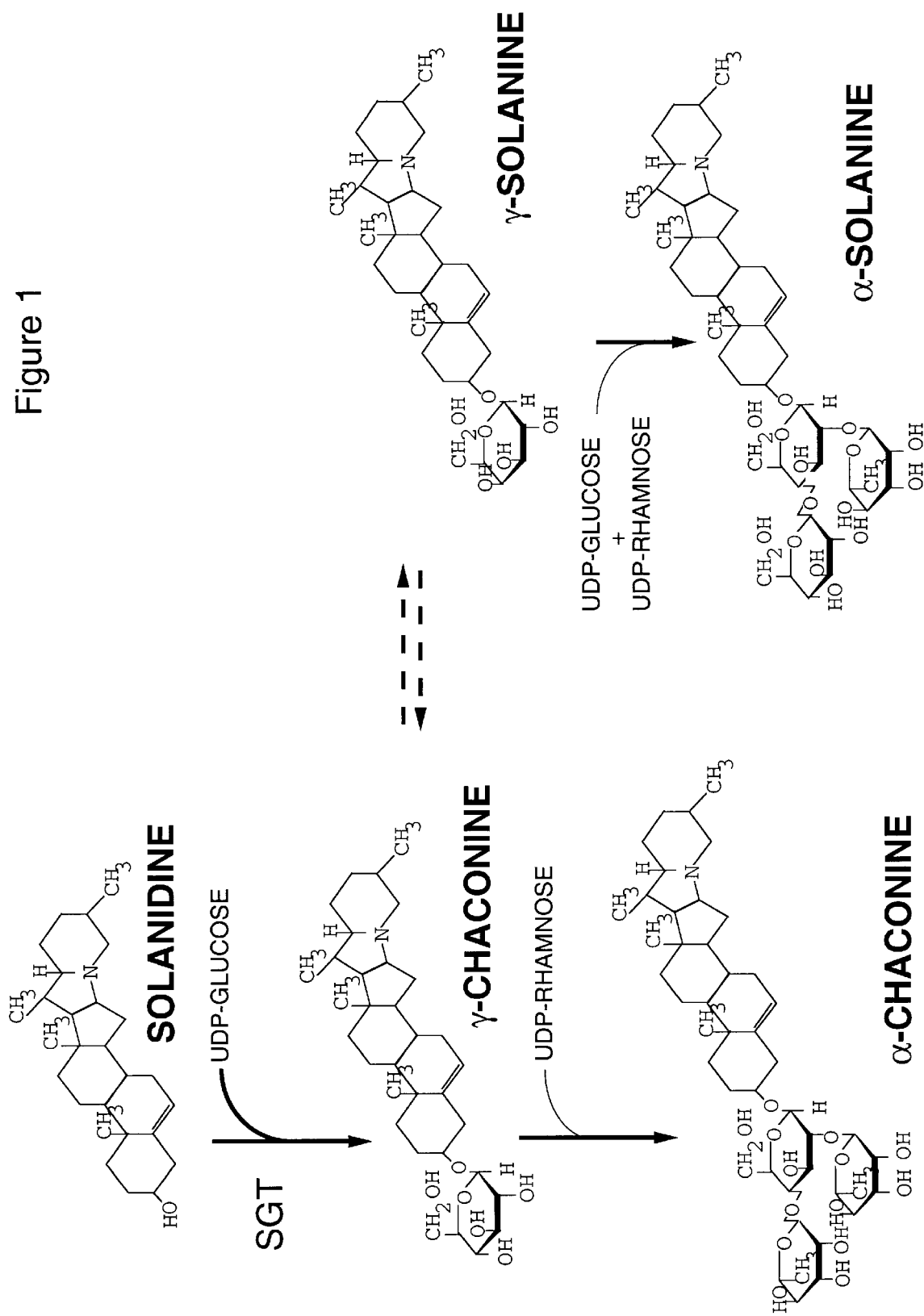
FIG. 1 shows a simplified biochemical pathway depicting SGT-catalyzed UDP-glucose glucose dependent glucosylation of solanidine to produce γ-chaconine and biosynthesis of the glycoalkaloids α-chaconine and α-solanine.

The present invention provides DNA sequences, in purified and isolated form, which encode SGT. For purposes of this invention, the term SGT (solanidine UDP-glucose glucosyltransferase) is defined to mean the enzyme which carries out the UDP-glucose dependent conversion of the aglycone solanidine to V-chaconine. Because SGT has the potential to play an important role in the regulation of glycoalkaloid accumulation in potato tubers, the partially purified enzyme has been characterized by a number of laboratories (Stapleton et al., 1991, supra, and Stapleton et al., Prot. Expr. Purif. 3:85–92 (1992); Bergenstrahle et aL, 1992, supra,; Packowski and Wojciechowski, 1994, supra; Zimowski, 1990, supra). However, purification of SGT to a degree that would allow sequence analysis and cloning has proved to be an elusive goal (Stapleton et al.,1992, supra).

The present invention also encompasses methods to obtain isolated DNA sequences having the characteristics described above. As discussed in detail below in the Examples, one method is to clone potato SGT by selection in yeast. Yeast expression libraries have been used to isolate cDNAs encoding a wide variety of plant enzymes employing strategies based either upon complementation (Dewey et al., Plant Cell 6:1495–1507 (1994); Bassham et al., Proc. Nati. Acad. Sci. USA 92:7262–7266 (1995)), screening (Corey et al., Proc. Natl. Acad. Sci. USA 90:11628–11632 (1993)) or selection on growth-inhibiting compounds (Kushnir et aL, Proc. Natl. Acad. Sci. 92:10580–10584 (1995)). The selection used here was based on the differential toxicity of aglycons and associated glycosylated forms (Roddick, Phytochemistry 13:9–15 (1974)). A cDNA encoding SGT was selected from a yeast expression library using a positive selection based on the higher toxicity of steroidal alkaloid aglycons relative to their associated glycosylated forms.

The identity of this cDNA as encoding SGT is established both by sequence similarity to previously described UDP-glycosyltransferases and by the characterization of the activity of the recombinant enzyme in yeast. The highly conserved nature of the UDP-glucose binding domain among evolutionarily divergent glycosyltransferases (Hundle et al., Proc. Nati. Acad. Sci USA 89:9321–9325 (1992); Yadav and Brew, J. Biol. Chem. 265:14163–14169 (1990)) allows unambiguous assignment to this family of the enzyme encoded by the cDNA described here (FIG. 4). In addition, the amino terminal domain of potato SGT shares significant similarity with previously described plant glycosyltransferases (FIG. 3). Perhaps the most unexpected result of the database comparisons (Altschul et al., J. Mol. Biol. 215:403410 (1990)) carried out with this clone was the identification of a putative steroid-binding domain in the deduced amino acid sequence. In contrast to the amino terminal and UDP-glucose domains which preferentially identified glycosyltransferases from plants, only mammalian glucuronosyltransferases were returned after computational searching the available database with the 34 residue peptide shown in FIG. 5. Of the returned loci for which substrates are defined, the high-scoring matches represent domains from steroid-specific enzymes.

The availability of the CDNA encoding potato SGT makes accessible both the genomic sequence which provides SGT and closely related enzymes found in the same plant, i.e., potato, as well as other cDNAs encoding SGT from other solanaceous plants. The cDNAs or portions thereof are used as probes to hybridize to the additional genomic or cDNA sequences by hybridization under stringent conditions. Sequences which hybridize specifically to a SGT coding sequence or its complement under stringent conditions are encompassed by the invention. For the purposes of this invention, stringent conditions are defined to mean that hybridization is due to at least about 70% homology, as opposed to nonspecific binding. Homology is defined to mean that the nucleotides match over the defined length of a selected region. Stringent conditions are described in T. Maniatis et al., Molecular Cloning: A Laboratory Manual, Cold Spring Harbor Laboratory, 1982 and DNA Cloning: A Practical Approach, Volumes I and 11 (Ed. D. N. Glover) IRL Press, Oxford, 1985.

A DNA coding sequence of SGT can also be prepared synthetically from overlapping oligonucleotides whose sequence contains codons for the amino acid sequence of SGT. Such oligonucleotides are prepared by standard methods and assembled and used to isolate the desired SGT gene.

Isolated DNA sequences which encode SGT may also be obtained by hybridization using an oligonucleotide probe capable of detecting a nucleotide sequence which codes for SGT. Such oligonucleotides are prepared by standard methods and assembled by procedures known to those is the art. The length of the probe employed must be sufficient to hybridize to homologous regions of DNA under stringent conditions. Generally it is recognized in the art that probes from about 17 to about 20 base pairs are of sufficient length to identify homologous sequences. Probes greater than 20 base pairs are more effective.

A DNA sequence which encodes SGT can be used to prepare recombinant DNA molecules (constructs) containing a sequence which encodes SGT, for example, recombinant vectors, such as cloning or expression vectors. A recombinant DNA molecule is prepared by cloning a DNA sequence which encodes SGT into any suitable vector that is capable of introducing a foreign gene into a heterologous host such as a bacterium, a yeast, a virus or its host organism, or in plants.

When the recombinant DNA molecule contains the DNA sequence encoding SGT or a fragment thereof in a 3' to 5' orientation under the control of a suitable promoter such as the Cauliflower Mosaic Virus 35S promoter, the construction is referred to as an antisense transgene. Such transgenes are introduced into hosts by various means, including electroporation, biolistic particle delivery systems, microinjection, transformation, or transfection. Efficacy of the introduced construct is determined by measuring immediate effects produced by transient expression of the introduced molecule or, as is the case in transgenic plants, by DNA-mediated expression of antisense constructs which have been stably introduced into the genome of the host. Suppression of SGT activity lowers the level of glycoalkaloids in plants which have been transformed with an antisense transgene.

Methods of inhibiting SGT production in a cell which normally produces SGT are also encompassed by the invention. For example, as discussed above and in detail below, one method is to modify the cell to contain an antisense nucleotide sequence complementary to an mRNA-encoding SGT. Plants or plant cells transformed with an antisense nucleotide sequence complementary to an mRNA-encoding SGT have reduced levels of toxic glycoalkaloids.

Isolation and purification of SGT presented problems of unusual difficulty. This enzyme is present at an extremely low level. The amount of SGT in SGT-enriched tissue is only about 0.001% of total protein. Other difficulties were present because SGT is inherently unstable and copurifies with the major storage protein patatin during isolation. Earlier attempts (Stapleton et al., 1991, supra) to isolate SGT were hampered by the small amounts of enzyme present in potato tissue and by the enzyme's instability during purification.

While we (Stapleton et aL, 1991 and 1992, supra) and others (Bergenstrahle et al. 1992, supra; Packowski and Wojciechowski, 1994, supra; Zimowski, 1990, supra) have reported partial purification of SGT from Solanaceous plants, attempts at purification to an extent that allows sequence analysis and cloning of appropriate cDNAs have so far proved unsuccessful. For this reason we employed an alternative cloning strategy based upon selection in yeast to isolate an SGT encoding cDNA from potato.

Differential toxicity of solanaceous alkaloid aglycons and their associated glycosides has been reported in both mammals (Osman, Phytochemistry 19:2599–2601 (1980)) and fungi (Roddick, 1974, supra). Characterization of the sensitivity of *Saccharomyces cerevisiae* to these secondary metabolites revealed significantly greater toxicity of the aglycons. Although the aglycons screened showed different levels of toxicity (tomatidine>osolasodine>solanidine), glycosylated derivatives were considerably less toxic. The differential toxicity in yeast of the aglycones and glycosylated forms was used to set up a positive selection for SGT in this heterologous system as described below.

The synthesis of glycoalkaloids of potato is known to involve a complex series of reactions and interactions that is incompletely understood. A number of enzymes including SGT are thought to be involved in the biosynthetic pathway. It is not clear to what extent the control of only one of these enzymes would be successful in controlling glycoalkaloid biosynthesis. Thus, it was not known to what extent the control of SGT production, taken alone, would be adequate to control the biosynthesis of glycoalkaloids. However, as illustrated in Example 3 and Table 1, below, control of SGT reduced glycoalkaloid content in transgenic plants.

DEFINITIONS

Solanidine UDP-glucose glycosyltransferase (SGT)

As defined herein, "SGT" includes all enzymes which are capable of catalyzing the UDP-glucose dependent conversion of the aglycone solanidine to γ-chaconine. The amino acid sequence of the enzyme may or may not be identical with the amino acid sequence which occurs naturally in solanaceous plants. In addition, artificially induced mutations are also included so long as they do not destroy activity. The definition of SGT used herein includes these variants which are derived by direct or indirect manipulation of the disclosed sequences.

It is also understood that the primary structure may be altered by post-translational processing or by subsequent chemical manipulation to result in a derivatized protein which contains, for example, glycosylation substituents, oxidized forms of, for example, cysteine or proline, conjugation to additional moieties, such as carriers, solid supports, and the like. These alterations do not remove the protein from the definition of SGT so long as its capacity to catalyze the UDP-glucose dependent conversion of the aglycone solanidine to y-chaconine is maintained.

Thus, the identity of an enzyme as "SGT" can be confirmed by its ability to carry out SGT enzyme activity. Such an assay is described in Example 2, below.

While alternative forms of assessment of SGT can be devised, and variations on the above protocol are certainly permissible, the foregoing provides a definite criterion for the presence of SGT activity and classification of a test protein as SGT.

Preferred forms of SGT of the invention include those illustrated herein and those derivable by systematic mutation of the genes. Such systematic mutation may be desirable to enhance the SGT properties of the enzyme, to enhance the characteristics of the enzyme which are ancillary to its activity, such as stability, or shelf life, or may be desirable to provide inactive forms useful in the control of SGT activity in vivo, as further described below.

As described above, "SGT" refers to a protein having the activity assessed by the assay set forth below; a "mutated SGT" refers to a protein which does not necessarily have this activity, but which is derived by mutation of a DNA encoding an SGT. By "derived from mutation" is meant both direct physical derivation from a DNA encoding the starting material SGT using, for example, site specific mutagenesis or indirect derivation by synthesis of DNA having a sequence related to, but deliberately different from, that of the SGT. As means for constructing oligonucleotides of the required length are available, such DNAs can be constructed wholly or partially from their individual constituent nucleotides.

SGT DNA Coding Sequences

SGT DNA coding sequence includes all DNA sequences in purified and isolated form which encode a SGT meeting the above definition. DNA sequences which hybridize specifically to a SGT coding sequence or its complement under stringent conditions are also encompassed by the present invention. As discussed above, stringent conditions are defined to mean that hybridization is due to at least about 70% homology over a selected region, as opposed to non-specific binding. For encoding SGT, the sequences should have 70% homology over 500 base pairs, preferably 70% homology over 700 base pairs, and more preferably 70% homology over 1000 base pairs.

Recombinant DNA Molecules

As used herein, "recombinant" refers to a nucleic acid sequence which has been obtained by manipulation of genetic material using restriction enzymes, ligases, and similar recombinant techniques as described by, for example, T. Maniatis et al.,1982, supra, and *DNA Cloning: A Practical Approach,* 1985, supra. "Recombinant," as used in the present application, does not refer to naturally-occurring genetic recombinations.

A recombinant DNA molecule refers to a hybrid DNA sequence comprising at least two DNA sequences, the first sequence not normally being found together in nature with the second. Examples include recombinant vectors, such as cloning or expression vectors which contain a DNA sequence encoding SGT which is in a 5' to 3' (sense) orientation or in a 3' to 5' (antisense) orientation. Example 1, below, describes preparation of an SGT recombinant DNA molecule.

The DNA sequences of the invention are also useful to prepare recombinant DNA expression molecules by cloning the sequence in any suitable expression vector using known techniques. The recombinant vector is constructed so that the coding sequence is located in the vector with the appropriate control sequence and operationally associated therewith, that is, the positioning and orientation of the SGT DNA coding sequence with respect to the control sequences are such that the coding sequence is transcribed under the control of the control sequences (i.e., by RNA polymerase which attaches to the DNA molecule at the control sequences). The control sequences may be ligated to the coding sequence prior to insertion into a vector. Alternatively, the coding sequence can be cloned directly into an expression vector which already contains the control sequence and an appropriate restriction site downstream from the control sequence. The vector should be selected so as to have a promoter operable in the host cell into which the vector is to be inserted (that is, the promoter should be recognized by the RNA polymerase of the host cell).

Expression Systems

A recombinant DNA expression molecule containing a sequence which encodes SGT in the 5' to 3' orientation is inserted into a host cell for expression of SGT. A variety of expression systems and hosts are known in the art for production of an enzyme. Examples of prokaryotic hosts are *Escherichia coli* and other bacterial hosts such as *B. subtilis* or Pseudomonas. Typical bacterial promoters include the trp, lac, tac, and β-lactamase promoters. A large number of recombinant systems have been developed for expression in eukaryotic hosts, including yeast, insect cells, mammalian cells, and plant cells. These systems are well characterized, and require the ligation of the coding sequence under the control of a suitable transcription initiating system (promoter) and, if desired, termination sequences and enhancers. For production of SGT, host cells transformed by a recombinant DNA expression molecule are grown, and the protein isolated from the host cells. The selection of appropriate growth conditions and recovery methods are within the skill of the art.

For expression in yeast, a library of wound-induced potato tuber cDNA was introduced and the yeast transformants were selected on solasodine-containing medium. Resistance to the alkaloid indicated the presence of SGT.

The coding sequence for SGT and the DNA which represents the reverse transcript of the mRNA that is subsequently translated into SGT can be included in expression systems suitable for plants.

Transformation of solanaceous plants which normally produce SGT, e.g., potato and tomato, with a recombinant expression system for the relevant SGT or a truncated form thereof may result, through an unknown mechanism, in suppression of the native production of SGT, and may thus provide a means to inhibit, for example, the biosynthesis of glycoalkaloids in such plants. This phenomenon has been referred to as "cosuppression". It has been shown previously that attempts to overexpress chalcone synthase in pigmented petunia petals by introducing the recombinant gene resulted in a suppression of the homologous native genes, thus resulting in a block in biosynthesis (C. Napoli et al., The Plant Cell 2: 279–289 (1990)). These results were confirmed and extended to transformation with genes encoding dihydroflavonol4-reductase genes in petunias by A. R. van der Krol et al., The Plant Cell 2: 291–299 (1990). It has also been found that transformation of a partial nopaline synthase gene into tobacco suppresses the expression of the endogenous corresponding gene, as reported by D. R. Goring et aL., Proc. Nati. Acad. Sci. USA 88: 1770–1774 (1991). In general, it appears that supplying a truncated form of the relevant gene in the "sense" orientation suppresses the endogenous expression of the native gene, thus lowering the level of the gene product, despite the presence of the additional expressed gene coding sequences.

Alternatively, a DNA which is transcribed into the complement of mRNA that is translated by the host plant into SGT can be provided to effect an antisense retardation of expression of the native gene.

Especially useful in connection with the SGT genes of the present invention are expression systems which are operable in plants. These include systems which are under control of a tissue-specific promoter, as well as those which involve promoters that are operable in all plant tissues.

Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, seed-specific promoters, etc. can also be used.

The cauliflower mosaic virus (CaMV) 35S promoter has been shown to be highly active in many plant organs and during many stages of development when integrated into the genome of transgenic plants.

Organ-specific promoters are also well known. For example, the patatin class I promoter is transcriptionally activated only in the potato tuber and can be used to target gene expression in the tuber (M. Bevan, Nucleic Acids Research 14: 46254636 (1986)). The granule-bound starch synthase (GBSS) promoter is also a potato-specific promoter (R.G.R. Visser et al, Plant Molecular Biology 17:691–699 (1991)).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in P. Goldberg, Trans R Soc London B314: 343 (1986)).

For expression in plants, the recombinant expression cassette will contain in addition to the SGT, a plant promoter region, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

For in situ production of the antisense mRNA of SGT, those regions of the SGT gene which are transcribed into SGT mRNA, including the untranslated regions thereof, are inserted into the expression vector under control of the promoter system in a reverse orientation. The resulting transcribed mRNA is then complementary to that normally produced by the plant. The presence of the antisense mRNA, as shown in Table 1, effectively reduces glycoalkaloid biosynthesis.

TABLE 1

Effect of Antisense Solanidine Glucosyltransferase Expression on Tuber Glycoalkaloid Levels in Transgenic Potato Clones

| Sample | Total Glyco-alkaloid* (Aberdeen) | % Wild Type (Aberdeen) | Total Glyco-alkaloid* (Albany) | % Wild Type (Albany) |
|---|---|---|---|---|
| Wild Type (Lenape) | 79 | 100 | 164 | 100 |
| Len35S#7 | 57 | 72 | 73 | 44 |
| Len35S#8 | 32 | 40 | NA | NA |
| LenGBSS#6 | 87 | 109 | 84 | 51 |
| LenGBSS#10 | 43 | 54 | NA | NA |
| LenGBSS#11 | 32 | 41 | 56 | 33 |
| LenGBSS#12 | 22 | 28 | NA | NA |

*mg/100 g fresh wt.

Table 1 shows the glycoalkaloid content in potato tubers from transgenic potato clones expressing antisense solanidine glucosyltransferase (SGT) mRNA. Two SGT antisense cassettes were employed, in which the antisense RNA was transcribed from either a Cauliflower Mosaic Virus 35S (35S) promoter or a tuber-specific Granule Bound Starch Synthase (GBSS) promoter. These constructs were introduced into the potato cultivar Lenape and greenhouse-grown mini-tubers were analyzed at Aberdeen, Ind. (Aberdeen) or at Albany, Calif. (Albany). The standard colorometric assay (Fitzpatrick et al., American Potato Journal 51:318–323 (1974)) was used at Aberdeen and a HPLC based method (Friedman et al., J Agric Food Chem 40:2157–2163 (1992)) was employed in Albany.

The resulting expression system or cassette is ligated into or otherwise constructed to be included in a recombinant vector which is appropriate for plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

In addition, vectors can also be constructed that contain in-frame ligations between the sequence encoding the SGT protein and sequences encoding other molecules of interest resulting in fusion proteins, by techniques well known in the art.

When an appropriate vector is obtained, transgenic plants are prepared which contain the desired expression system. A number of techniques are known in the art for transformation of plants or plant cells.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (J. Schell, Science 237: 1176–1183 (1987)). Ti and Ri plasmids contain two regions essential for the production of transformed cells.

Construction of recombinant Ti and Ri plasmids in general follows methods typically used with the more common bacterial vectors, such as pUC19. There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al. (EMBO J 3: 1681–1689 (1984)) and the non-oncogenic Ti plasmid pGV3850 described by Zambryski et al. (EMBO J 2: 2143–2150 (1983)). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan (Nucleic Acids Research 12: 8711–8721 (1984)) and the non-oncogenic Ti plasmid PAL4404 described by Hoekema et al. (Nature 303: 179–180 (1983)). Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons or potato tuber discs, can be transformed by Agrobacterium and (b) that the transformed cells or tissues can be induced to regenerate into whole plants. Most dicot species can be transformed by Agrobacterium as all species which are a natural plant host for Agrobacterium are transformable in vitro.

Identification of transformed cells or plants is generally accomplished by including a selectable marker in the transforming vector, or by obtaining evidence of successful bacterial infection.

Plant cells which have been transformed can be regenerated using known techniques. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. II, 1986). It is known that practically all plants can be regenerated from cultured cells or tissues.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable. The regenerated plants are transferred to standard soil conditions and cultivated in a conventional manner.

After the expression cassette is stably incorporated into regenerated transgenic plants, it can be transferred to other plants by sexual crossing. Any of a number of standard breeding techniques can be used, depending upon the species to be crossed. The plants are grown and harvested using conventional procedures.

Antisense Expression

When the SGT gene or a fragment thereof is cloned into a heterologous expression vector in the opposite orientation (e.g. in the 3' to 5' orientation) to that found in nature, an antisense construct is created. Transcription of the antisense region of such a construct results in the production of an RNA molecule complementary to the messenger RNA (mRNA) of the gene or genes being targeted. The activity of such a construct in either transient or stable DNA-mediated transformation systems results in the inhibition of SGT activity with subsequent reduction of SGT activity or glycoalkaloid levels in the plant or system containing the construct. The antisense SGT portion of the construct must be of sufficient size to provide the desired inhibitory effect. As few as 52 bases of 5' untranslated antisense RNA has been shown to inhibit enzymatic activity in some systems (J. G. Izant and H. Weitraub, Science 229: 345–352 (1985)). The sequence complementary to a sequence of the messenger RNA will usually be at least 50 nucleotides, preferably about 100 nucleotides or more and may include the entire length of the coding region.

Similarly, a gene or a fragment thereof or multiple copies of the fragments can be cloned into a heterologous expression system in the native orientation and cause co-suppression or inhibition of an indigenous enzyme (C. Napoli, C. Lemieux, and R. Jorgensen, The Plant Cell 2: 279–289 (1990); C. J. S. Smite et al., Molec. Gen. Genet. 224: 477–481 (1990); and A. R. van der Krol et al., The Plant Cell 2: 291–299 (1990)).

The antisense constructs are useful to inhibit SGT activity in plants which normally produce SGT, e.g., potato and tomato, and thereby reduce glycoalkaloid levels. Example 3, below, illustrates that glycoalkaloid biosynthesis in potatoes can be controlled and inhibited by antisense expression of the SGT coding sequence supplied in a construct under the control of the Cauliflower Mosaic Virus 35S and GBSS promoters.

Numerous issued U.S. Patents are available which disclose information useful to those skilled in the art in practicing the present invention. U.S. Pat. No. 4,710,463 to Murray discloses recombinant DNA expression vectors incorporating DNA sequences coding for a foreign polypeptide, e.g., Hepatitis B virus antigens, in a unicellular host. U.S. Pat. No. 4,440,859 to Rutter et al. discloses recombinant bacterial plasmids containing the coding sequences of higher organisms. U.S. Pat. No. 4,652,525 to Rutter et al. discloses isolation of a nucleotide coding sequence having the structure of the reverse transcript of an mRNA which encodes insulin, synthesis of double stranded DNA having the sequence, and transfer of the DNA to a host microorganism. U.S. Pat. No. 4,546,082 to Kudjan and Herskowitz discloses methods for expression of biologically useful heterologous polypeptides in yeast. U.S. Pat. No. 4,582,800 to Crowl discloses expression vectors which utilize transcriptional regulatory elements derived from bacteriophage lambda. U.S. Pat. No. 4,363,877 to Goodman and Seeburg discloses isolation of cDNA transcripts complementary to isolated mRNA, and recombinant DNA vectors containing codons for human somatomammotropin and for human growth hormone. U.S. Pat. No. 4,601,980 to Goeddel and Heyneker discloses the expression of a gene coding for human growth hormone in a pBR322/*E. coli* system. U.S. Pat. No. 4,590,163 to Helinski and Ditta discloses PK2 plasmids useful for gene cloning in gram-negative bacteria such as *E. coli*. U.S. Pat. No. 4,237,224 to Cohen and Boyer discloses methods for producing recombinant DNA expression vectors. U.S. Pat. Nos. 4,468,464 and 4,740,470 to Cohen and Boyer describe biologically functional molecular chimeras. U.S. Pat. No. 4,940,838 to Schilperoort and Hoekema describes a process for the incorporation of foreign DNA Into the genome of dicotyledonous plants. U.S. Pat. No. 4,332,897 to Nakano et al. discloses lamboid bacteriophage vectors useful for transforming *E. coli*. U.S. Pat. No. 4,332,901 to Goldstein discloses a P4 derivative bacteriophage cloning vector. U.S. Pat. No. 4,704,362 to Itakura and Riggs and U.S. Pat. No. 4,356,270 to Itakura disclose recombinant plasmid vectors useful for transforming microbial hosts. U.S. Pat. No. 4,273,875 to Manis discloses a plasmid designated PUC6 useful as a cloning vector for transforming microbial hosts. U.S. Pat. No. 4,349,629 to Carey et al. discloses plasmid vectors employing the trp bacterial promoter useful as recombinant DNA expression vectors. U.S. Pat. No. 4,362,817 to Reusser discloses the plasmid pUC1060, which contains a tet gene promoter, useful as an expression vector. U.S. Pat. Nos. 4,565,785 and 4,411,994 by Gilbert et al. discloses a recombinant DNA molecule having a bacterial gene and non-bacterial gene encoding a selected polypeptide. U.S. Pat. No. 4,683,195 by Mullin describes a process for amplifying nucleic acid sequences. U.S. Pat. No. 4,801,540 by Hiaft et al. discloses a DNA sequence encoding polygalacturonase (PG) and its use to modulate PG expression in plant cells. U.S. Pat. No. 5,107,065 by Shewmaker et al. discloses antisense regulation of gene expression in plant cells. U.S. Pat. No. 5,168,064 by Bennett et al describes a method of inhibiting endo-1,4-b-glucanase activity in plants using antisense DNA constructions. U.S. Pat. No. 5,073,676 to Bridges et al. describes tomato antisense pectin esterase. U.S. Pat. 5,034,323 by Jorgensen et al. describes a method for altering color patterns of flowers and other plant parts. The disclosures of all U.S. patent references cited herein are to be incorporated herein by reference.

EXAMPLES

The following examples are intended only to further illustrate the invention and are not intended to limit the scope of the invention which is described by the claims.

EXAMPLE 1

Selection of SGT cDNA in Yeast

A yeast expression vector library containing cDNAs from wounded tuber tissue was constructed in *E. coli*. Yeast (*Saccharomyces cerevisiae*) strain KT1115 (MATα, leu2-3, leu2-112, ura3-52) (Dewey et al., Plant Cell 6:1495–1507 (1994)) was cultured on YPD medium (Sherman, Methods Enzymol. 194:3–20 (1991)). Growth of KT1 115 on SGAs and associated aglycons was assessed by plating the strain on YPGal (YP-2% galactose) medium incorporating various dilutions of alkaloids or SGAs prepared as 1–10 mM stock solutions in ethanol. Solanidine, solasodine, tomatidine and α-chaconine were purchased from Sigma. Gamma chaconine was prepared by partial acid hydrolysis of α-chaconine and HPLC purification as described by Friedman etal. (J. Agric. Food Chem. 41:1397–1406 (1993)).

A yeast expression library of wound-induced potato tuber cDNAs was prepared by excising cDNA inserts from a previously constructed λgt11 library (Garbarino et al., Plant Mol. Biol. 20:235–244 (1992)) with BamH1 and ligating them into the pYES2 expression vector (Invitrogen). The ligation mixture was transformed into *E. coli* strain DH5α by electroporation. Twenty random clones were analyzed by restriction digestion to confirm the presence of inserts. In the pYES2 expression vector employed, introduced sequences are transcribed from a gal1 galactose-inducible promoter. The library was introduced into KT 1115 as described by Gietz et al. (Nucl. Acids Res. 20:1425 (1992)) and selected on minimal medium lacking uracil. Yeast transformants (>10,000) were then replica plated onto galactose containing medium with or without 50 μM solasodine. After one week, colonies growing on the solasodine-containing medium were transferred to minimal medium lacking uracil to ensure maintenance of the plasmid. Four of the approximately $10^4$ colonies screened were selected for analysis based upon apparent growth in the presence of the alkaloid. Plasmid DNA was prepared from the yeast (Strathern and Higgins, Methods Enzymol. 194:302–318 (1991)) and transformed into *E. coli*. Ability to confer resistance to solasodine toxicity was confirmed by re-transformation of KT 115 following amplification in *E. coli*. Following transformation into KT 115, only one of the plasmids was found to confer resistance to the alkaloid. The observed resistance was dependent upon the presence of galactose as a carbon source.

Sequence Analysis of Potato SGT

Figure 2A:
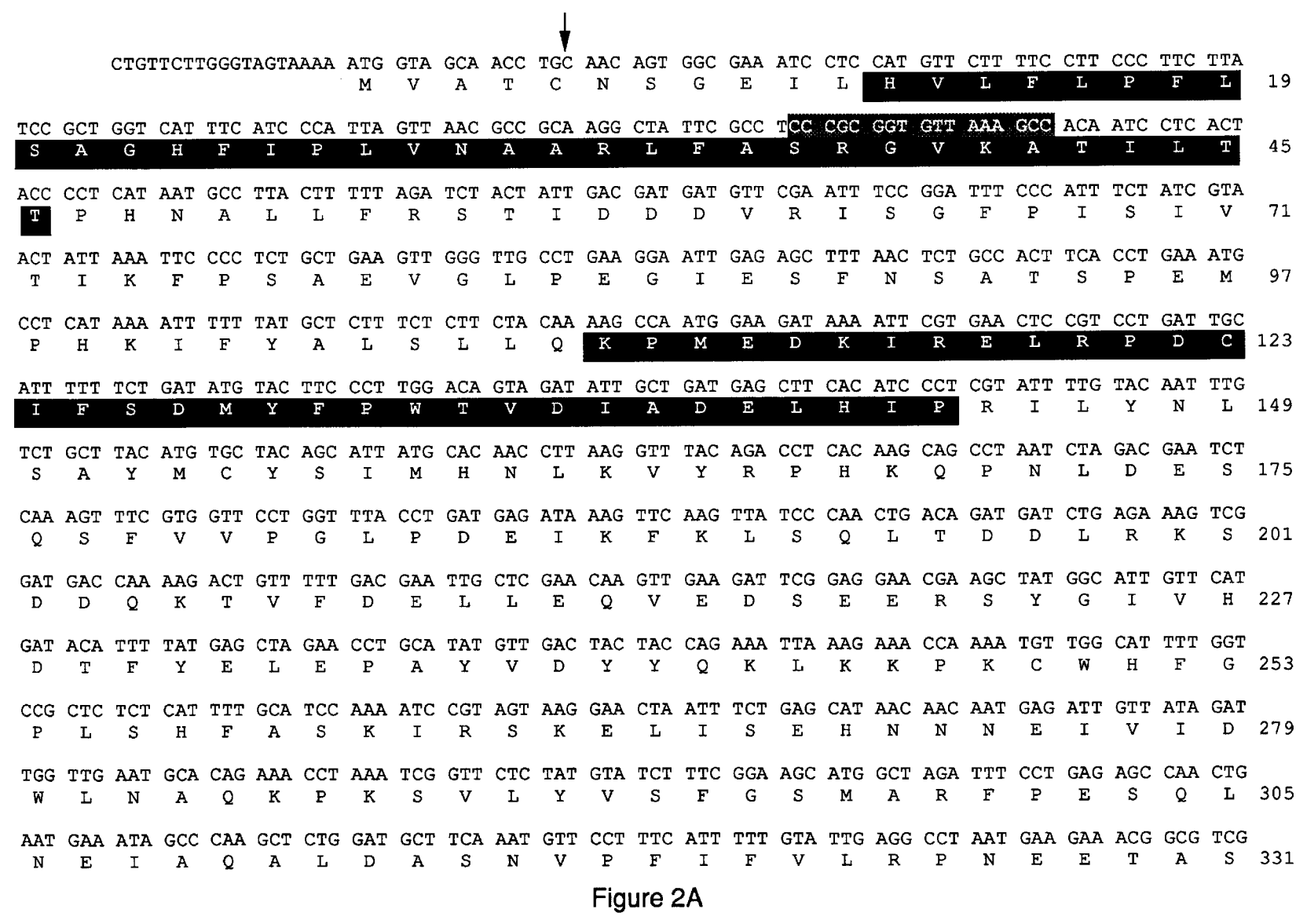

The selected cDNA, designated StSGT, was 1578 bp in length and contained an open reading frame encoding a 483 residue polypeptide that appeared to lack an initiator methionine (FIG. 2). In order to obtain additional 5' sequence, a potato tuber λgt11 library (Garbarino et al., 1992, supra) was used as a template in PCR amplification with one StSGT specific primer and a second primer located within the λ vector (FIG. 2). Inserts from positive pYES2 clones were subcloned into pUC1 9 and sequenced using the fmol DNA sequencing system of Promega™. Sequence analysis of the longest clone resulted in 34 bp of additional sequence 5' to the original StSGT isolate that encoded a potential initiator methionine (FIG. 2). The shaded deduced amino acid sequences indicate conserved domains associated with the amino terminus (see FIG. 3), the putative steroid binding site (see FIG. 5) and the UDP-glucose binding site (see FIG. 4). The arrow indicates the 5' end of the original StSGT cDNA clone. Additional 5' sequence was obtained using a primer complementary to the shaded DNA sequence.

A database search (Altschul et aL, 1990, supra) with the deduced StSGT coding sequence revealed significant similarity to previously characterized UDP-glycosyltransferases from both eukaryotic and prokaryotic species. FIG. 3 shows a comparison of the amino acid sequences of the amino terminal domains of UDP-glycosyltransferases. The deduced amino acid sequence of potato SGT (StSGT) is compared to amino terminal sequences of an anthocyanidin UDP-rhamnosyltransferase from petunia (PhART, GenBank assession # S33169), a maize IAA glucosyltransferase (IAAGT, GenBank assession # A54739) and a rhamnosyltransferase from Pseudomonas aerugenosa (ParRT, GenBank locus B53652). Numbers indicate position relative to the putative initiator methionine. Residues highlighted in black indicate positions of identity. Shaded residues indicate conservative substitutions. FIG. 4 shows a comparison of the amino acid sequences of the UDP binding domain of UDP-glycosyltransferases. The deduced amino acid sequence of potato SGT (StSGT) is compared to sequences of a UDP-glucosyltransferase from cassava (CasGT, GenBank assession # S41951), IAAGT and PhART as in FIG. 3, and maize bronze-1 (MzBzl, GenBank Locus UFO3). Numbering, highlighting and alignments were determined as in FIG. 3. FIG. 5 shows a comparison of a putative steroid-binding domain of three steroid-specific mammalian UDP-glucuronosyltranferases and potato SGT (StSGT). The deduced amino acid sequence of SGT is compared to sequences of human 3,4-catechol estrogen-specific (Hudb7, GenBank assession # P16662) and polyhydroxylated estrogen-specific (Hudbb, GenBank assession# P36538) enzymes, and a rat β-hydroxysteroid UDP-glucuronosyltransferase (Rudb6, GenBank assession # P19488). Numbering, highlighting and alignments were determined as in FIG. 3. Regions of high similarity to other plant UDP-glycosyltransferases were observed in both the amino- (FIG. 3) and carboxyl-terminal (FIG. 4) domains of the deduced amino acid sequence. An alignment of the StSGT putative UDP-glucose binding domain (Hundle et al., 1992, supra; Yadav and Brew, 1990, supra) to a selection of plant UDP-glycosyltransferases is shown in FIG. 4. In contrast to these domains, a database search with an internal sequence (residues 110–143) revealed similarity to a series of steroid-specific UDP-glucuronosyltranferases from mammals (FIG. 5), with no significant similarity to previously described plant enzymes. The sequence alignment shown in FIG. 5 suggests that this domain represents a part of a steroid binding domain in these enzymes. The observed similarities of the StSGT deduced amino acid sequence to previously described transferases suggest that this cDNA encodes a UDP-glycosyltransferase that glycosylates steroid-related substrates.

EXAMPLE 2

Recombinant SGT Enzyme Activity in Yeast

Characterization of the recombinant potato SGT in yeast required partial purification to remove competing UDP-glucose hydrolyzing enzymes, also required for analysis of SGT activity in potato tissue. Yeast cells containing pStSGT or pYES2 were grown in liquid culture YNB-Glucose to 0.8 $OD_{595}$/ml then centrifuged (5.3K×g, 5min, 4° C.) to pellet the cells. The pellet was washed in sterile water, recentrifuged and suspended in 10 ml YPA-Galactose media then transferred into 250 ml of YPA-Gal and grown to 3.0 $OD_{595}$/ml. The washed YPA-Gal cells were permeabilized by resuspending the pellet in cold extraction buffer (20 mM Bis-Tris propane, pH 7.7, 5 mM $MgCl_2$, 1 mM DTT, 0.05% Triton X-100, and 0.1 mM PMSF), 100 mg wet pellet /mi. This material was placed in liquid nitrogen for 1 Omin then held overnight at −80° C. (Miozzari, Anal. Biochem. 90:220–233 (1978)). The thawed sample was centrifuged (20K×g, 10 min, 4° C.), and the resulting supernatant was further purified to evaluate SGT activity.

Characterization of authentic potato SGT in crude extracts indicated the necessity for an initial anion-exchange chromatography purification step prior to SGT activity determinations. This was confirmed with yeast extracts derived from pStSGT containing cells. Lysate supernatants (1 5 mg/30 ml) were loaded onto a 5 ml BioRad Econo-Q-cartridge pre-equilibrated with 50 ml of extraction buffer (minus Triton X-100 and PMSF). The nonbinding material was washed from the cartridge with 30 ml of extraction buffer at a flow rate of 2.0 ml/min. Proteins were eluted with a 0.25M KCl step gradient at a 2.0 ml/min flow rate. One minute fractions were collected and 200 μl aliquots were assayed for enzyme activity using 10 μl of 1 mM of the aglycons solanidine, solasodine, tomatidine in DMSO or DMSO alone with 80 μl of 100 mM Bis-Tris propane buffer, pH 6.6, plus 10 μl of UDP-[$^3$H-glucose] (Stapleton et al., 1991, supra).

Characterization of the substrate specificity of SGT purified from potato demonstrated that the endogenous enzyme glucosylates tomatidine and solasodine at rates significantly higher than solanidine (solasodine>tomatidine>solanidine). Similarly, the recombinant enzyme from yeast glucosylated solanidine at a rate lower than the other two aglycons. However, in contrast to the endogenous enzyme, the recombinant SGT glucosylated tomatidine at a rate greater than was observed for solasodine. No SGT activity was observed in extracts prepared from *S. cerevisiae* containing the empty vector, pYES2, controls.

Figures 6A, 6B:
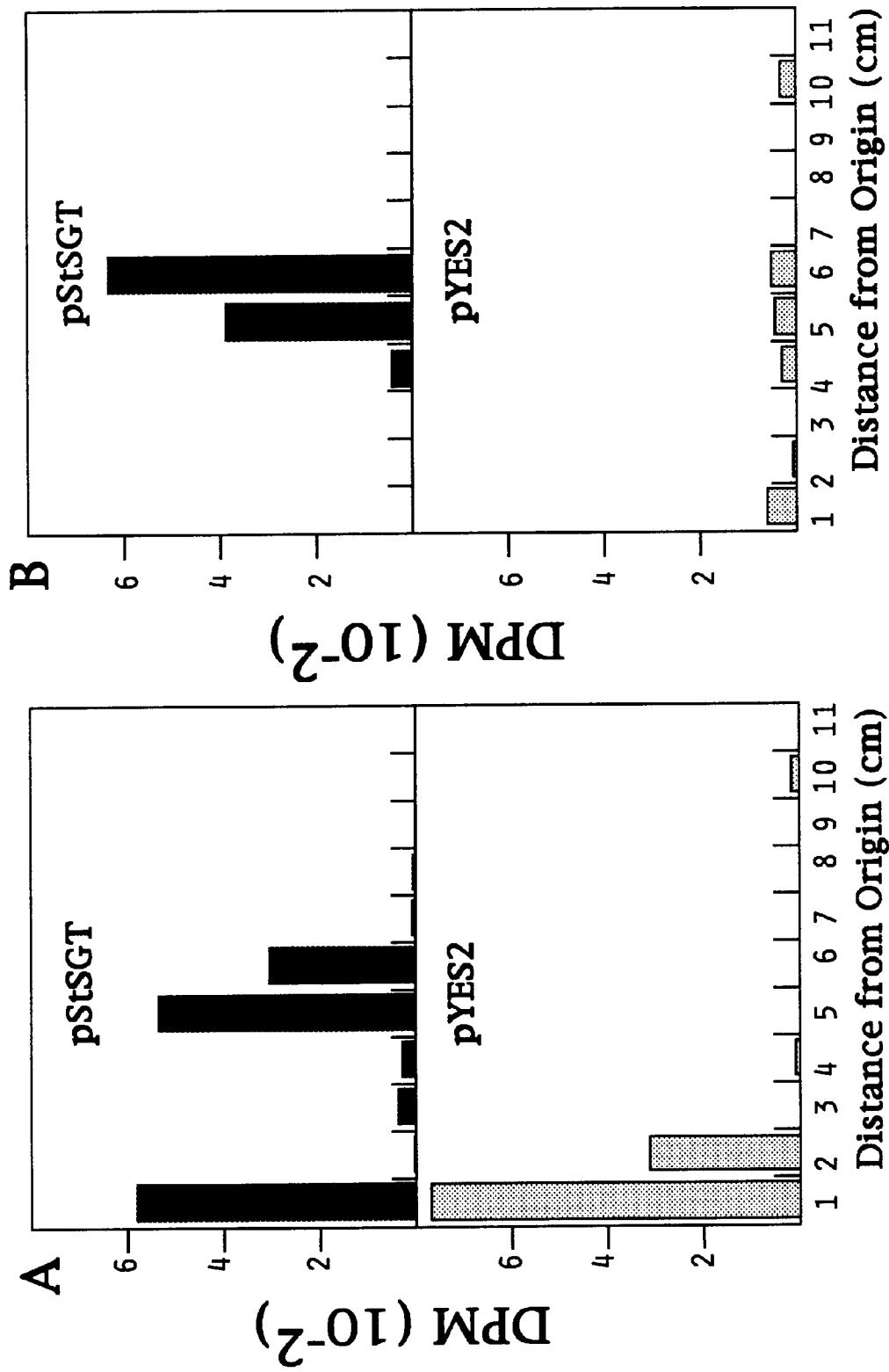
FIGS. 6A–6B show the SGT activity of recombinant SGT reaction products in the presence of (A) UDP-[$^3$H-glucose] and (B) $^3$H-dihydrosolasodine.

In order to verify the identity of the recombinant SGT reaction products, samples generated using either UDP-[$^3$H-glucose] or $^3$H-dihydrosolasodine as substrates were analyzed by TLC (FIGS. 6A and 6B). The UDP-[$^3$H-glucose] assays were incubated for 30 minutes as described previously (Stapleton et al., 1991, supra) and the remaining assay supernatant, approximately 200 μl, was lyophilized and extracted two times with 10 μl of methanol and then analyzed by TLC. $^3$H-dihydrosolasodine was prepared by reduction of solasodine with tritium gas (American Radiolabeled Chemicals Inc., St. Louis, Mo.). For the $^3$H-dihydrosolasodine assay, 10 mM UDP-glucose was substituted for the UDP-[$^3$H-glucose] and the 300 μl final volume was lyophilized and extracted two times with 10 μl of methanol and then analyzed 7by TLC. The TLC was performed on Merck precoated silica gel 60 plates in a saturated chamber of chlorform:methanol:2% NH$_4$OH, 70:30:5. One centimeter sections were scraped from the plates and analyzed by scintillation counting. The plates were then briefly dipped in Calcofluor 0.02%-methanol (Jellema et al., J. Chrom. 176:435439 (1979)) to determine the distance from the origin, (cm/R$_f$), for solanidine (9.1/0.83), solasodine (9.3/0.85), and γ-chaconine (5.9/0.54). The radioactive peaks were then compared to the two aglycons and the glycosylated solanidine product.

For both substrates, radiolabeled reaction products migrated to positions indistinguishable from authentic γ-chaconine. Synthesis of these reaction products was dependent upon the presence of the StSGT cDNA insert and was not observed in the pYES2 controls (FIGS. 6A and 6B).

EXAMPLE 3

The following example describes the transformation of potato plants with clone StSGT (1578 bp) in an antisense orientation.

Construction of Antisense SGT Chimeric Plasmids and Use in Transgenic Potatoes

Figure 7:
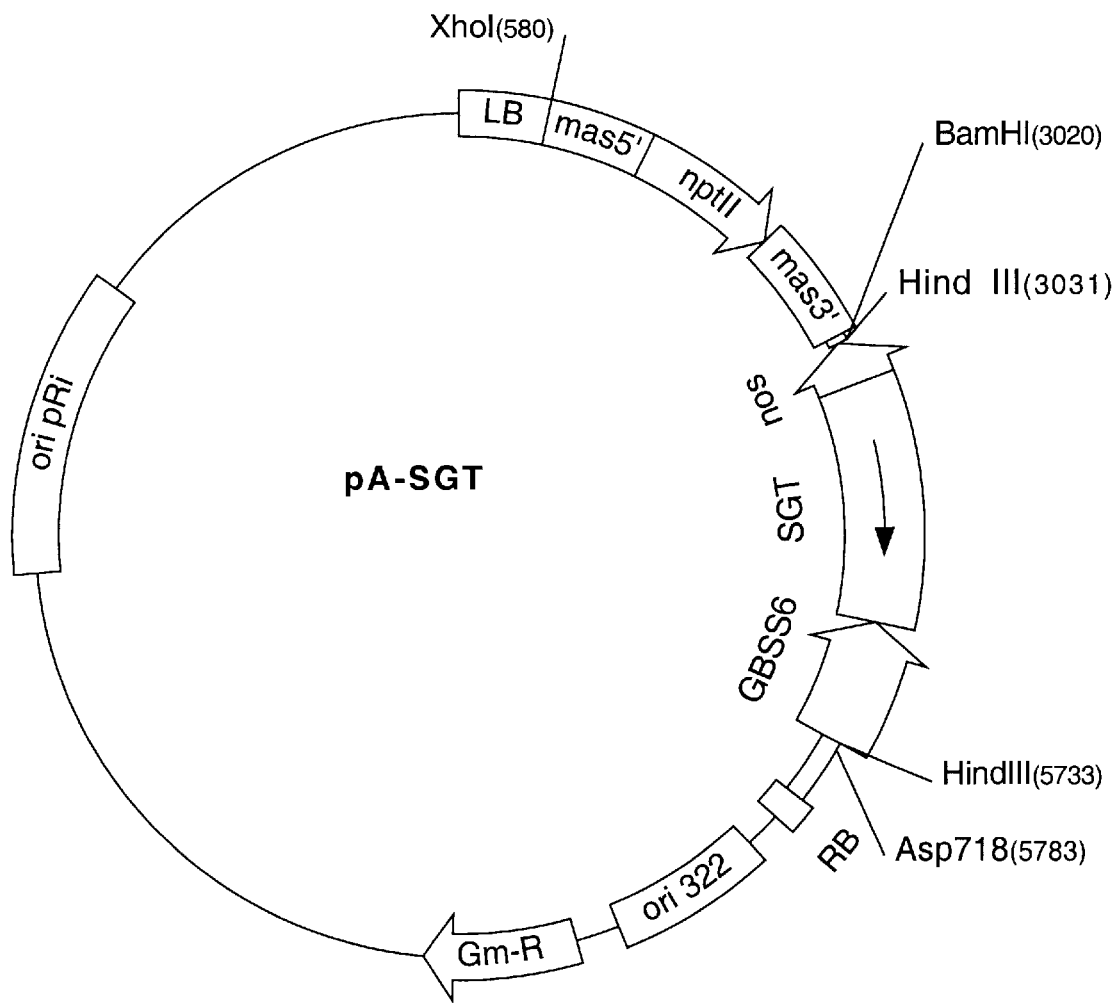
FIG. 7 shows the plasmid pA-SGT containing antisense SGT and the GBSS promoter.

The 1578 bp fragment was excised from plasmid StSGT with the restriction endonuclease BamHI. After purifying the fragment with "Geneclean II" (Bio 101), it was cloned into plasmid pARS201 to form a chimera consisting of the Cauliflower Mosaic Virus 35S promoter or the GBSS promoter fused to the partial SGT sequence in an antisense orientation followed by the nopaline synthase (nos) terminator region from plasmid pBI 121 (Bevan et al., Nucleic Acids Research 1 1: 369–385 (1983). The 35S and GBSS transgenes were subsequently removed intact as a HindIII fragment and cloned into plasmid pCGN1547 (McBride and Summerfelt, Plant Molecular Biology 14: 269–276 (1990)). The restriction map of the resulting SGT binary antisense plasmid pA-SGT is shown in FIG. 7. The plasmid was transformed into *E. coli* strain TB-1 and, after confirming the orientation of the SGT insert, it was transformed into *Agrobacterum tumefasciens* strain PC2760 (An et al., EMBO J. 4: 277–284 (1985)). The binary vector pCGN1547 contains the neomycin phosphotransferase (nptll) gene (Bevan et al., Nucleic Acids Research 12: 8711–8721 (1984)) which confers kanamycin resistance, and expression in the plants is driven by the mannopine synthase promoter. Cultures of PC2760 harboring the modified binary vector pA-SGT were grown at 29° C. in liquid Luria-Bertain (LB) broth supplemented with 20 mg/L gentamycin. Four hours before microtuber inoculation, 50 μm 3',5'-dimethoxy4'-hydroxyacetophenone (acetosyringone) (Aldrich Chemical Co.) was added to the 50 ml Agrobacterum culture.

Transformations

Potato microtubers were transformed with the antisense plasmid using an Agrobacterium-mediated procedure described in Snyder et al., Plant Cell Reports, 12:324–327 (1993), which is incorporated herein by reference.

Green-house grown mini-tubers were transformed with antisense plasmids containing either the Cauliflower Mosaic Virus 35S promoter or the Granule Bound Starch Synthase promoter (see Table 1).

Transgenic material is being propagated for planting, and the mature field-grown tubers will be analyzed using either the colorometric or HPLC methods, as described above.

---

What is claimed is:

1. An isolated nucleic acid molecule selected from the group consisting of:
   (a) SEQ ID NO: 1;
   (b) the RNA equivalent of SEQ ID NO: 1;
   (c) the complement of the molecule defined in (a) or (b); and
   (d) a molecule that encodes potato solanidine UDP-glucose glucosyltransferase (SGT).

2. The isolated nucleic acid molecule of claim 1, wherein said molecule is an antisense nucleotide sequence complementary to an mRNA that encodes SGT.

3. A recombinant nucleic acid molecule comprising the isolated nucleic acid molecule of claim 1.

4. A recombinant DNA molecule comprising the nucleic acid molecule of claim 1 which is transcribed to form RNA, wherein said RNA inhibits production of SGT in a plant or plant cell in which said nucleic acid molecule is transcribed, and wherein said nucleic acid molecule is operably linked to control sequences which effect its transcription into said RNA.

5. The recombinant DNA molecule of claim 4 wherein said nucleic a molecule is in the 3' to 5' orientation.

6. A recombinant DNA molecule comprising a nucleic acid sequence which encodes SGT, said sequence comprising the nucleic acid sequence of SEQ ID NO:1 or comprising a nucleic acid sequence that encodes the amino acid sequence of SEQ ID NO:2.

7. The recombinant DNA molecule of claim 6 which is an expression vector having a promoter, wherein said nucleic acid sequence is inserted in said vector downstream of said promoter and operatively associated therewith.

8. The recombinant DNA molecule of claim 7 wherein said promoter is a Granule Bound Starch Synthase (GBSS) promoter.

9. A cell transformed with the recombinant DNA molecule of claim 7.

10. A cell transformed with the recombinant DNA molecule of claim 8.

11. A transgenic plant prepared by transforming plant cells with the recombinant DNA molecule of claim 4 to obtain transformed plant cells and regenerating a transgenic plant from said transformed plant cells.

12. The transgenic plant of claim 11 which is potato or tomato.

13. A method of inhibiting SGT production in a plant cell which comprises transforming said plant cell with a nucleic acid molecule selected from the group consisting of:
   (a) a nucleic acid molecule encoding the SGT of SEQ ID NO:2: and
   (b) an antisense nucleic acid molecule complementary to an mRNA encoding the SGT of SEQ ID NO:2.

14. The method of claim 13, wherein said nucleic acid molecule is in an expression vector.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1607 base pairs
      (B) TYPE: nucleic acid
      (C) STRANDEDNESS: single (D) TOPOLOGY: linear (ii) MOLECULE TYPE: cDNA to mRNA (iii) HYPOTHETICAL: NO (iv) ANTI-SENSE: NO (vi) ORIGINAL SOURCE:
    (A) ORGANISM: Solanum tuberosum
    (B) STRAIN: cv. Lemhi Russet
    (C) INDIVIDUAL ISOLATE: SGT1750
    (D) DEVELOPMENTAL STAGE: mature, somatic
    (F) TISSUE TYPE: tuber (vii) IMMEDIATE SOURCE:
    (A) LIBRARY: lambda gt11 cDNA library
    (B) CLONE: SGT 1750

(ix) FEATURE:
    (A) NAME/KEY: CDS
    (B) LOCATION: 20..1486
    (D) OTHER INFORMATION: /product= "solanidine glucosyltransferase"

(x) PUBLICATION INFORMATION:
    (A) AUTHORS: Moehs, Charles P.
              Allen, Paul V.
              Friedman, Mendel
              Belknap, William R.
    (B) TITLE: Cloning and expression of solanidine UDP-glucose glucosyltransferase from potato
    (C) JOURNAL: The Plant Journal
    (D) VOLUME: 11
    (E) ISSUE: 2
    (G) DATE: 1997
    (K) RELEVANT RESIDUES IN SEQ ID NO:1: FROM 1 TO 488

(xi) SEQUENCE DESCRIPTION: SEQ ID NO:1:

```
CTGTTCTTGG GTAGTAAAA ATG GTA GCA ACC TGC AAC AGT GGC GAA ATC CTC        52
                    Met Val Ala Thr Cys Asn Ser Gly Glu Ile Leu
                     1               5                      10

CAT GTT CTT TTC CTT CCC TTC TTA TCC GCT GGT CAT TTC ATC CCA TTA        100
His Val Leu Phe Leu Pro Phe Leu Ser Ala Gly His Phe Ile Pro Leu
            15                  20                  25

GTT AAC GCC GCA AGG CTA TTC GCC TCC CGC GGT GTT AAA GCC ACA ATC        148
Val Asn Ala Ala Arg Leu Phe Ala Ser Arg Gly Val Lys Ala Thr Ile
        30                  35                  40

CTC ACT ACC CCT CAT AAT GCC TTA CTT TTT AGA TCT ACT ATT GAC GAT        196
Leu Thr Thr Pro His Asn Ala Leu Leu Phe Arg Ser Thr Ile Asp Asp
    45                  50                  55

GAT GTT CGA ATT TCC GGA TTT CCC ATT TCT ATC GTA ACT ATT AAA TTC        244
Asp Val Arg Ile Ser Gly Phe Pro Ile Ser Ile Val Thr Ile Lys Phe
60                  65                  70                  75

CCC TCT GCT GAA GTT GGG TTG CCT GAA GGA ATT GAG AGC TTT AAC TCT        292
Pro Ser Ala Glu Val Gly Leu Pro Glu Gly Ile Glu Ser Phe Asn Ser
                80                  85                  90

GCC ACT TCA CCT GAA ATG CCT CAT AAA ATT TTT TAT GCT CTT TCT CTT        340
Ala Thr Ser Pro Glu Met Pro His Lys Ile Phe Tyr Ala Leu Ser Leu
            95                 100                 105

CTA CAA AAG CCA ATG GAA GAT AAA ATT CGT GAA CTC CGT CCT GAT TGC        388
Leu Gln Lys Pro Met Glu Asp Lys Ile Arg Glu Leu Arg Pro Asp Cys
        110                 115                 120

ATT TTT TCT GAT ATG TAC TTC CCT TGG ACA GTA GAT ATT GCT GAT GAG        436
Ile Phe Ser Asp Met Tyr Phe Pro Trp Thr Val Asp Ile Ala Asp Glu
    125                 130                 135

CTT CAC ATC CCT CGT ATT TTG TAC AAT TTG TCT GCT TAC ATG TGC TAC        484
Leu His Ile Pro Arg Ile Leu Tyr Asn Leu Ser Ala Tyr Met Cys Tyr
140                 145                 150                 155
```

```
AGC ATT ATG CAC AAC CTT AAG GTT TAC AGA CCT CAC AAG CAG CCT AAT       532
Ser Ile Met His Asn Leu Lys Val Tyr Arg Pro His Lys Gln Pro Asn
            160                 165                 170

CTA GAC GAA TCT CAA AGT TTC GTG GTT CCT GGT TTA CCT GAT GAG ATA       580
Leu Asp Glu Ser Gln Ser Phe Val Val Pro Gly Leu Pro Asp Glu Ile
        175                 180                 185

AAG TTC AAG TTA TCC CAA CTG ACA GAT GAT CTG AGA AAG TCG GAT GAC       628
Lys Phe Lys Leu Ser Gln Leu Thr Asp Asp Leu Arg Lys Ser Asp Asp
            190                 195                 200

CAA AAG ACT GTT TTT GAC GAA TTG CTC GAA CAA GTT GAA GAT TCG GAG       676
Gln Lys Thr Val Phe Asp Glu Leu Leu Glu Gln Val Glu Asp Ser Glu
        205                 210                 215

GAA CGA AGC TAT GGC ATT GTT CAT GAT ACA TTT TAT GAG CTA GAA CCT       724
Glu Arg Ser Tyr Gly Ile Val His Asp Thr Phe Tyr Glu Leu Glu Pro
220                 225                 230                 235

GCA TAT GTT GAC TAC TAC CAG AAA TTA AAG AAA CCA AAA TGT TGG CAT       772
Ala Tyr Val Asp Tyr Tyr Gln Lys Leu Lys Lys Pro Lys Cys Trp His
            240                 245                 250

TTT GGT CCG CTC TCT CAT TTT GCA TCC AAA ATC CGT AGT AAG GAA CTA       820
Phe Gly Pro Leu Ser His Phe Ala Ser Lys Ile Arg Ser Lys Glu Leu
        255                 260                 265

ATT TCT GAG CAT AAC AAC AAT GAG ATT GTT ATA GAT TGG TTG AAT GCA       868
Ile Ser Glu His Asn Asn Asn Glu Ile Val Ile Asp Trp Leu Asn Ala
        270                 275                 280

CAG AAA CCT AAA TCG GTT CTC TAT GTA TCT TTC GGA AGC ATG GCT AGA       916
Gln Lys Pro Lys Ser Val Leu Tyr Val Ser Phe Gly Ser Met Ala Arg
        285                 290                 295

TTT CCT GAG AGC CAA CTG AAT GAA ATA GCC CAA GCT CTG GAT GCT TCA       964
Phe Pro Glu Ser Gln Leu Asn Glu Ile Ala Gln Ala Leu Asp Ala Ser
300                 305                 310                 315

AAT GTT CCT TTC ATT TTT GTA TTG AGG CCT AAT GAA GAA ACG GCG TCG      1012
Asn Val Pro Phe Ile Phe Val Leu Arg Pro Asn Glu Glu Thr Ala Ser
            320                 325                 330

TGG TTG CCA GTT GGT AAT TTA GAG GAC AAG ACT AAA AAG GGT TTG TAC      1060
Trp Leu Pro Val Gly Asn Leu Glu Asp Lys Thr Lys Lys Gly Leu Tyr
        335                 340                 345

ATC AAA GGG TGG GTC CCA CAG CTT ACG ATC ATG GAA CAT TCA GCA ACA      1108
Ile Lys Gly Trp Val Pro Gln Leu Thr Ile Met Glu His Ser Ala Thr
        350                 355                 360

GGC GGG TTC ATG ACT CAT TGT GGT ACT AAT TCG GTT CTG GAA GCC ATC      1156
Gly Gly Phe Met Thr His Cys Gly Thr Asn Ser Val Leu Glu Ala Ile
        365                 370                 375

ACT TTT GGC GTG CCA ATG ATA ACA TGG CCA CTT TAT GCT GAT CAA TTC      1204
Thr Phe Gly Val Pro Met Ile Thr Trp Pro Leu Tyr Ala Asp Gln Phe
380                 385                 390                 395

TAC AAC GAG AAG GTA GTC GAG GTT AGG GGA TTG GGA ATC AAA ATC GGG      1252
Tyr Asn Glu Lys Val Val Glu Val Arg Gly Leu Gly Ile Lys Ile Gly
            400                 405                 410

ATA GAT GTA TGG AAT GAA GGG ATT GAG ATC ACG GGC CCT GTA ATA GAA      1300
Ile Asp Val Trp Asn Glu Gly Ile Glu Ile Thr Gly Pro Val Ile Glu
            415                 420                 425

AGC GCC AAG ATT AGA GAA GCA ATT GAG AGA CTA ATG ATC AGT AAT GGT      1348
Ser Ala Lys Ile Arg Glu Ala Ile Glu Arg Leu Met Ile Ser Asn Gly
        430                 435                 440

TCT GAG GAA ATT ATA AAT ATT AGG GAT AGA GTA ATG GCT ATG AGC AAA      1396
Ser Glu Glu Ile Ile Asn Ile Arg Asp Arg Val Met Ala Met Ser Lys
        445                 450                 455

ATG GCT CAG AAT GCA ACA AAT GAA GGT GGA TCT TCG TGG AAC AAT CTC      1444
Met Ala Gln Asn Ala Thr Asn Glu Gly Gly Ser Ser Trp Asn Asn Leu
460                 465                 470                 475
```

-continued

```
ACT GCT CTC ATT CAA CAT ATC AAG AAT TAT AAT CTT AAT TAGTTGAAGA    1493
Thr Ala Leu Ile Gln His Ile Lys Asn Tyr Asn Leu Asn
                480                 485

CAGAAATAAG TCCTTGCATT GTAACATGGT GTGTGTGTGT GTTTTTTTTC CACTTAATAA 1553

AATGAAGGAA TGGATGGATG GATGGATCTT AACTTTAAAA AAAAAAAAAA AAAA       1607
```

(2) INFORMATION FOR SEQ ID NO:2:

(i) SEQUENCE CHARACTERISTICS:
        (A) LENGTH: 488 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Ala Thr Cys Asn Ser Gly Glu Ile Leu His Val Leu Phe Leu
 1               5                  10                  15

Pro Phe Leu Ser Ala Gly His Phe Ile Pro Leu Val Asn Ala Ala Arg
                20                  25                  30

Leu Phe Ala Ser Arg Gly Val Lys Ala Thr Ile Leu Thr Thr Pro His
            35                  40                  45

Asn Ala Leu Leu Phe Arg Ser Thr Ile Asp Asp Val Arg Ile Ser
    50                  55                  60

Gly Phe Pro Ile Ser Ile Val Thr Ile Lys Phe Pro Ser Ala Glu Val
65                  70                  75                  80

Gly Leu Pro Glu Gly Ile Glu Ser Phe Asn Ser Ala Thr Ser Pro Glu
                85                  90                  95

Met Pro His Lys Ile Phe Tyr Ala Leu Ser Leu Leu Gln Lys Pro Met
                100                 105                 110

Glu Asp Lys Ile Arg Glu Leu Arg Pro Asp Cys Ile Phe Ser Asp Met
            115                 120                 125

Tyr Phe Pro Trp Thr Val Asp Ile Ala Asp Glu Leu His Ile Pro Arg
    130                 135                 140

Ile Leu Tyr Asn Leu Ser Ala Tyr Met Cys Tyr Ser Ile Met His Asn
145                 150                 155                 160

Leu Lys Val Tyr Arg Pro His Lys Gln Pro Asn Leu Asp Glu Ser Gln
                165                 170                 175

Ser Phe Val Val Pro Gly Leu Pro Asp Glu Ile Lys Phe Lys Leu Ser
                180                 185                 190

Gln Leu Thr Asp Asp Leu Arg Lys Ser Asp Asp Gln Lys Thr Val Phe
            195                 200                 205

Asp Glu Leu Leu Glu Gln Val Glu Asp Ser Glu Arg Ser Tyr Gly
    210                 215                 220

Ile Val His Asp Thr Phe Tyr Glu Leu Glu Pro Ala Tyr Val Asp Tyr
225                 230                 235                 240

Tyr Gln Lys Leu Lys Lys Pro Lys Cys Trp His Phe Gly Pro Leu Ser
                245                 250                 255

His Phe Ala Ser Lys Ile Arg Ser Lys Glu Leu Ile Ser Glu His Asn
                260                 265                 270

Asn Asn Glu Ile Val Ile Asp Trp Leu Asn Ala Gln Lys Pro Lys Ser
            275                 280                 285

Val Leu Tyr Val Ser Phe Gly Ser Met Ala Arg Phe Pro Glu Ser Gln
    290                 295                 300

Leu Asn Glu Ile Ala Gln Ala Leu Asp Ala Ser Asn Val Pro Phe Ile
305                 310                 315                 320
```

-continued

```
Phe Val Leu Arg Pro Asn Glu Glu Thr Ala Ser Trp Leu Pro Val Gly
            325                 330                 335

Asn Leu Glu Asp Lys Thr Lys Lys Gly Leu Tyr Ile Lys Gly Trp Val
            340                 345                 350

Pro Gln Leu Thr Ile Met Glu His Ser Ala Thr Gly Gly Phe Met Thr
        355                 360                 365

His Cys Gly Thr Asn Ser Val Leu Glu Ala Ile Thr Phe Gly Val Pro
    370                 375                 380

Met Ile Thr Trp Pro Leu Tyr Ala Asp Gln Phe Tyr Asn Glu Lys Val
385                 390                 395                 400

Val Glu Val Arg Gly Leu Gly Ile Lys Ile Gly Ile Asp Val Trp Asn
            405                 410                 415

Glu Gly Ile Glu Ile Thr Gly Pro Val Ile Glu Ser Ala Lys Ile Arg
            420                 425                 430

Glu Ala Ile Glu Arg Leu Met Ile Ser Asn Gly Ser Glu Glu Ile Ile
        435                 440                 445

Asn Ile Arg Asp Arg Val Met Ala Met Ser Lys Met Ala Gln Asn Ala
    450                 455                 460

Thr Asn Glu Gly Gly Ser Ser Trp Asn Asn Leu Thr Ala Leu Ile Gln
465                 470                 475                 480

His Ile Lys Asn Tyr Asn Leu Asn
            485
```